United States Patent [19]

DeLuca et al.

[11] Patent Number: 4,505,906

[45] Date of Patent: Mar. 19, 1985

[54] HYDROXYVITAMIN $D_2$ ISOMERS

[75] Inventors: Hector F. DeLuca; Heinrich K. Schnoes; Rafal R. Sicinski; Yoko Tanaka, all of Madison, Wis.

[73] Assignee: Wisconsin Alumni Research Foundation, Madison, Wis.

[21] Appl. No.: 575,115

[22] Filed: Jan. 30, 1984

[51] Int. Cl.³ .............................................. C07J 9/00
[52] U.S. Cl. ................................. 514/167; 260/397.2
[58] Field of Search ...................... 260/397.2; 424/236

[56] References Cited

U.S. PATENT DOCUMENTS 4,360,471 11/1982 DeLuca et al. .................. 260/397.2

Primary Examiner—Elbert L. Roberts
Attorney, Agent, or Firm—Howard W. Bremer

[57] ABSTRACT

The invention provides, as novel vitamin D derivatives, isomers of 25-hydroxyvitamin $D_2$ and 1α,25-dihydroxyvitamin $D_2$ characterized by a double bond at the 23,24-position.

The compounds are characterized by vitamin D-like activity as assessed by competitive binding assays and would therefore, find application as substitutes for vitamin D or various of its metabolites in their various known applications and in the treatment of vitamin D-responsive bone diseases.

4 Claims, No Drawings

HYDROXYVITAMIN $D_2$ ISOMERS

This invention was made with Government support under NIH Grants Nos. AM 14881 and AM-32701 awarded by the Department of Health and Human Services. The Government has certain rights in this invention.

TECHNICAL FIELD

This invention relates to biologically active vitamin D compounds.

More specifically, this invention relates to novel double-bond isomers of 25-hydroxyvitamin $D_2$ and $1\alpha,25$-dihydroxyvitamin $D_2$ characterized by a double bond in the 23,24-position.

BACKGROUND

Both vitamin $D_2$ and vitamin $D_3$, their hydroxylated metabolites, as well as some of their structural analogs are known as effective regulators of calcium and phosphate homeostasis in the animal or human. These compounds, therefore, have utility as therapeutic agents for the prevention and treatment of disorders of calcium and phosphate metabolism, such as rickets, osteodystrophy, osteomalacia, osteoporosis and related mineral imbalance conditions.

Known compounds of this class are characterized generally by a saturated steroid side chain (as in the vitamin $D_3$ series) or a 22-trans-unsaturated side chain with a 24-methyl substituent (as in the vitamin $D_2$ series). The compounds of the present invention are side chain-unsaturated, but are distinguished by the presence of a 23-trans-double bond from the known vitamin $D_2$ metabolites which include 25-hydroxyvitamin $D_2$ (U.S. Pat. No. 3,585,221), $1\alpha,25$-dihydroxyvitamin $D_2$ (U.S. Pat. No. 3,880,894) as well as the 24-hydroxy- and 24,25-dihydroxyvitamin $D_2$ compounds (Jones et al. Arch. Biochem. Biophys. 202, 450 (1980)).

Other vitamin $D_2$ structural analogs that have been prepared include $1\alpha$-hydroxyvitamin $D_2$ (U.S. Pat. No. 3,907,843), and certain side chain unsaturated compounds (Bogoslovskii et al. J. Gen. Chem. USSR 48(4), 828 (1978); U.S. Pat. No. 3,786,061) which, by virtue of containing 22,23-trans-double bond, may be considered 24-desmethyl derivatives of vitamin $D_2$. Another compound structurally related to the products of the present invention is 23-dehydro-25-hydroxyvitamin $D_3$(U.S. Pat. No. 4,360,471).

DISCLOSURE OF INVENTION

Novel vitamin D derivatives have now been prepared which are characterized by the structure

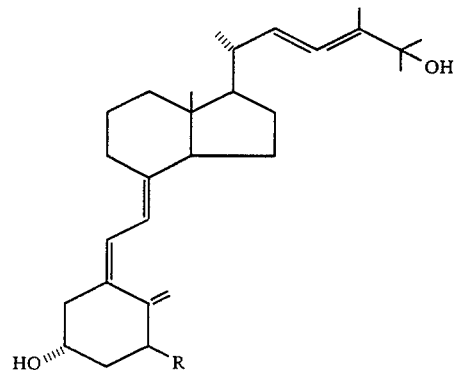

wherein R is hydrogen or a hydroxy group.

These compounds are thus isomers of 25-hydroxyvitamin $D_2$ and $1\alpha$, 25-dihydroxyvitamin $D_2$, respectively, characterized by the novel feature of having a 23,24-double bond in the side chain which results in a planar, rather than tetrahedral, orientation of the methyl substitutent on carbon 24.

BEST MODE OF CARRYING OUT THE INVENTION

The above compounds can be prepared by the following process:

The known keto-vitamin D analog ((24R/S)-25-oxo-27-norvitamin $D_2$) (I) of the structure shown below is used as starting material.

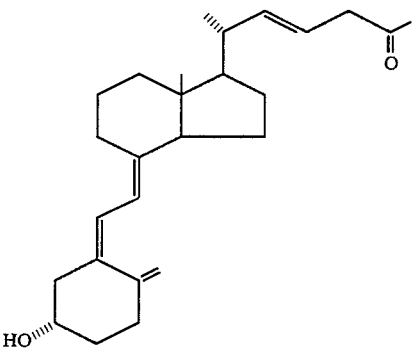

I

This material, which is available by the procedure of DeLuca et al. (co-pending application, Ser. No. 420,191, filed Sept. 20, 1982, allowed Dec. 30, 1983) is dissolved in anhydrous methanol (9 ml), to which is added 135 mg of $NaHCO_3$, and the mixture is stirred and heated at 50° C. for 6 h. After cooling and concentration in vacuo to ~1 ml the mixture is poured into water and extracted with benzene and ether. Organic extracts are combined, washed with water, dried ($Na_2SO_4$) and evaporated. The crude product is subjected to high performance liquid chromatography (2% 2-propanol/hexane, 6.2 mm×25 cm Zorbax-SIL column) to obtain 2.4 mg (80%) of the $\alpha,\beta$-unsaturated ketone (eluting at 45 ml) which is characterized by the following spectral data:

NMR $\delta$0.58 (3H, s, 18-$H_3$), 0.97 (3H, d, J=6.8 Hz, 21-$H_3$), 1.77 (3H, s, 28-$H_3$), 2.33 (3H, s,

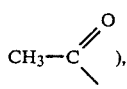

3.98 (1H, m, 3-H), 4.83 and 5.06 (2H, each narrow multiplets, 19-H$_2$), 6.05 and 6.25 (2H, ABq, J=12.0 Hz, 7-H and 6-H), 6.67 (1H, t, J=7.0 Hz, 23-H); UV (Et$_2$O) $\lambda_{max}$ 223 and 264 nm; UV (EtOH) $\lambda_{max}$ 236 and 263 nm; mass spectrum, m/e 396 (M$^+$, 33), 363 (M$^+$-H$_2$O-Me, 13), 253 (M$^+$-side chain-H$_2$O, 4), 136 (100), 118 (98). This $\alpha,\beta$-unsaturated ketone product has the structure II shown below:

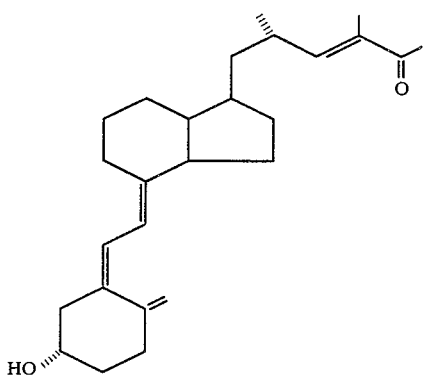

A solution of the above $\alpha,\beta$-unsaturated ketone in anhydrous ether (1 ml) is then treated with CH$_3$MgBr (2.85M sol. in ether) and the mixture is stirred for 2 h at room temperature. After quenching with saturated NH$_4$Cl, the solution is diluted with benzene and washed with water. The organic phase is separated, dried (Na$_2$SO$_4$) and evaporated. The crude product is purified by high performance liquid chromatography (6.2 mm×25 cm Zorbax-SIL column using 2% 2-propanol in hexane as an eluent). The desired product (eluting at 83 ml) has the structure III shown below:

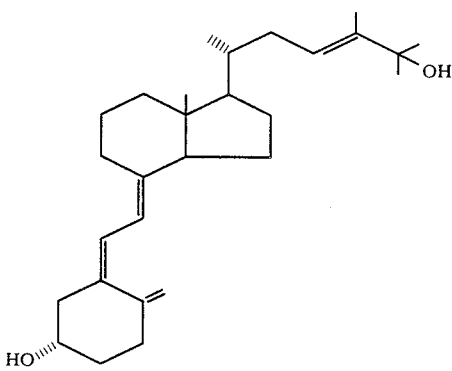

and is characterized by the following data:

NMR $\delta$: 0.56 (3H, s, 18-H$_3$), 0.91 (3H, d, J=7.0 Hz, 21-H$_3$), 1.34 (6H, s, 26- and 27-H$_3$), 1.59 (3H, s, 28-H$_3$), 3.96 (1H, m, 3-H), 4.83 and 5.06 (2H, each narr. m., 19-H$_2$), 5.50 (1H, t, J=7.0 Hz, 23-H), 6.04 and 6.25 (2H, ABq, J=11.9 Hz, 7-H and 6-H); UV (EtOH) $\lambda_{max}$ 265 nm, $\lambda_{min}$ 228 nm; mass spectrum, m/e 412 (M$^+$, 38), 394 (M$^+$-H$_2$O, 10), 379 (M$^+$-H$_2$O-Me, 15), 299 (C$_{20}$/C$_{22}$ cleavage, 5), 281 (299-H$_2$O, 9), 271 (M$^+$-side chain, 4), 253 (M$^+$-side chain-H$_2$O, 5), 136 (100), 118 (74).

The above $\Delta^{23}$-25-hydroxy compound can then be 1$\alpha$-hydroxylated by the general procedure of DeLuca et al. (U.S. Pat. Nos. 4,195,027, 4,260,549). The above product is first tosylated under conventional conditions to obtain the corresponding 3$\beta$-tosylate derivative. This 3$\beta$-tosylintermediate is then solvolyzed by heating in a solution of MeOH containing NaHCO$_3$ for 8.5 hr. at 55° C. to obtain the 3,5-cyclovitamin D derivative having structure IV shown below, where R=H:

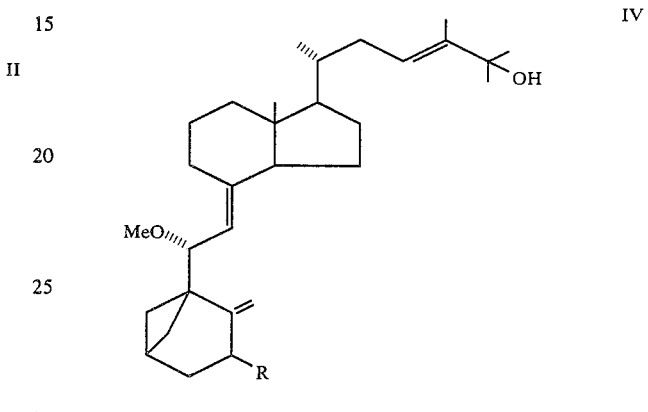

This 3,5-cyclovitamin D compound is then hydroxylated at carbon 1, by treatment with SeO$_2$ (0.45 molar equiv.) and tert.-BuOOH (1.2 molar equivalents) according to the procedure of DeLuca et al. (U.S. Pat. No. 4,195,027). After purification of high performance liquid chromatography or by thin layer chromatography, the desired 1$\alpha$,25-dihydroxy-3,5-cyclovitamin D intermediate which has the structure shown above where R=OH is obtained. This product is then solvolyzed by heating in glacial acetic acid at 55° C. for 15 min, to obtain in admixture the 5,6-cis-1$\alpha$,25-dihydroxyvitamin D derivative characterized by the structure shown below:

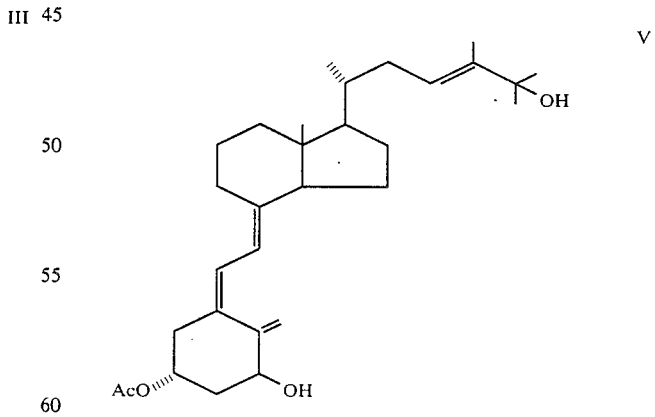

and the corresponding 5,6-trans-isomer. The above 5,6-cis3$\beta$-acetate derivative (V) is purified from the mixture by high pressure liquid chromatography, and then subjected to hydrolysis in mild base (e.g. 10% KOH in MeOH, 1 hr, 50° C.) to obtain the desired 1$\alpha$,25-dihydroxy-$\Delta^{23}$-vitamin D compound represented by structure VI below:

VI

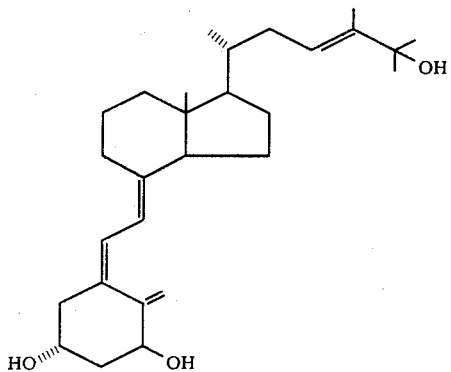

In the foregoing description the physiochemical data presented was obtained using the below-referenced methods and apparatus. High pressure liquid chromatography (HPLC) was performed on a Waters Associates Model ALC/GPC 204 using a Zorbax-Sil (DuPont) (6.2 mm×25 cm column, flow rate 4 ml/min, 1500 psi). Preparative thin-layer chromatography (TLC) was carried out on Silica 60 PF-254 (20×20 cm plates, 1 mm silica gel). All reactions are preferably performed under an inert atmosphere (e.g. argon).

If desired, the compounds of this invention can be readily obtained in crystalline form by crystallization from a suitable solvent such as hexane, ethers or alcohols (absolute or aqueous as applicable) or mixtures thereof as will be evident to and well understood by those skilled in the art.

The novel compounds of this invention exhibit biological activity as assessed by the competitive binding assays, conducted according to the procedure of Shepard et al. Biochem. J. 182, 55 (1979). In accordance with such assays it has been found, for example that the $\Delta^{23}$-25-hydroxy product, III, expresses activity equal to that of 25-hydroxyvitamin $D_3$, a known and potent vitamin $D_3$ metabolite. The present compounds would, therefore, find application as effective therapeutic agents in human or veterinary medicine, such as for the treatment of calcium-imbalance conditions and the known vitamin D-responsive bone diseases, as well as for the correction of mineral imbalance conditions in animals. Particularly preferred for such applications is the 1α-hydroxylated compound of this invention since the presence of a 1α-hydroxy group enhances the activity and efficacy of the vitamin.

For therapeutic applications the compounds may be formulated as pills, tablets, capsules or suppositories, together with acceptable pharmaceutical excipients, or as solutions, emulsions, dispersions or suspensions in innocuous and pharmaceutically acceptable solvents, oils or other carriers and may be administered by any known and conventional method, e.g. orally, or by injection, infusion, or dermal application, in amounts which will provide the recipient animal with from about 0.5 μg to about 10 μg per day, depending, of course, upon the animals size, medical history, condition and response.

I claim:

1. A compound having the formula

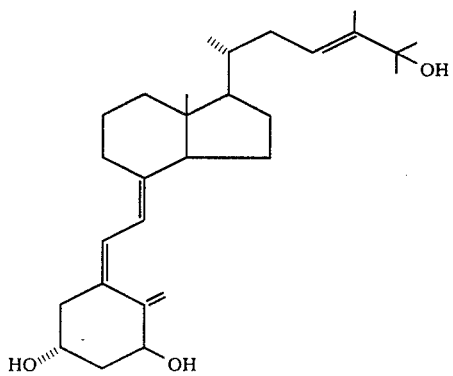

2. The compound of claim 1 in crystalline form.

3. A pharmaceutical composition comprising the compound of claim 1 and a pharmaceutically acceptable excipient.

4. A compound having the formula

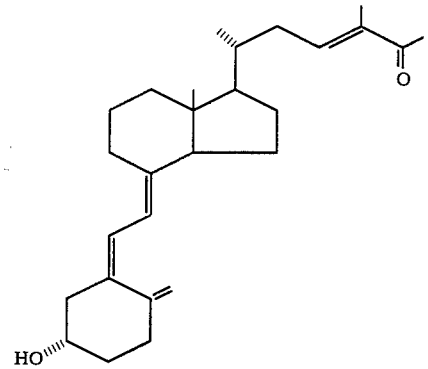

* * * * *